United States Patent
Rivier et al.

(10) Patent No.: US 9,889,126 B2
(45) Date of Patent: Feb. 13, 2018

(54) USE OF NARATRIPTAN IN THE TREATMENT OF ROSACEA

(71) Applicant: GALDERMA RESEARCH & DEVELOPMENT, Biot (FR)

(72) Inventors: Michel Rivier, Nice (FR); Isabelle Carlavan, Grasse (FR); Jerome Aubert, Grasse (FR)

(73) Assignee: GALDERMA RESEARCH & DEVELOPMENT, Biot (FR)

(*) Notice: Subject to any disclaimer, the term of this patent is extended or adjusted under 35 U.S.C. 154(b) by 0 days.

(21) Appl. No.: 15/105,084

(22) PCT Filed: Dec. 18, 2014

(86) PCT No.: PCT/FR2014/053440
§ 371 (c)(1),
(2) Date: Jun. 16, 2016

(87) PCT Pub. No.: WO2015/092309
PCT Pub. Date: Jun. 25, 2015

(65) Prior Publication Data
US 2017/0027922 A1    Feb. 2, 2017

(30) Foreign Application Priority Data
Dec. 19, 2013 (FR) .................. 13 62978

(51) Int. Cl.
*A61K 31/454* (2006.01)
*A61K 9/00* (2006.01)

(52) U.S. Cl.
CPC .......... *A61K 31/454* (2013.01); *A61K 9/0014* (2013.01)

(58) Field of Classification Search
CPC ................... A61K 31/454; A61K 9/0014
See application file for complete search history.

(56) References Cited

U.S. PATENT DOCUMENTS

2012/0252863 A1* 10/2012 Dascalu .............. A61K 9/0014
514/415

FOREIGN PATENT DOCUMENTS

| FR | 2758263 A1 | 7/1998 |
| WO | 2011/048496 A1 | 4/2011 |

OTHER PUBLICATIONS

International Search Report and Written Opinion dated Mar. 9, 2015 corresponding to International Patent Application No. PCT/FR2014/053440, 12 pages.
Spoendlin, J., et al., "Migraine, triptans, and the risk of developing rosacea," Journal of the Academy of Dermatology, vol. 69, No. 3, Sep. 2013, pp. 399-406.
Baldwin, H.E, "Diagnosis and Treatment of Rosacea: State of the Art," Journal of Drugs in Dermatology, SUNY Medical Center, NY, NY, vol. 11, No. 6, Jun. 2012, pp. 725-730.

* cited by examiner

*Primary Examiner* — Savitha Rao
(74) *Attorney, Agent, or Firm* — Dentons US LLP

(57) ABSTRACT

Described herein is a method of using a topical, pharmaceutical composition, particularly a dermatological composition, comprising naratriptan to treat rosacea and in particular erythematotelangiectatic rosacea.

16 Claims, 2 Drawing Sheets

USE OF NARATRIPTAN IN THE TREATMENT OF ROSACEA

CROSS-REFERENCE TO PRIOR APPLICATIONS

Figure 1:
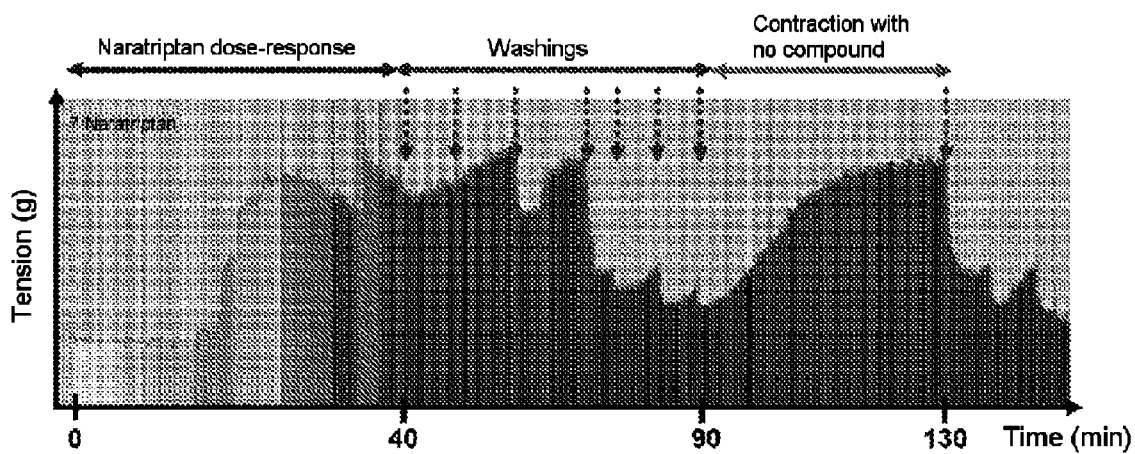

This application is a National Stage of PCT/FR2014/053440, filed Dec. 18, 2014, and designating the United States (published on Jun. 25, 2015, as WO 2015/092309 A1), which claims priority under 35 U.S.C. § 119 to French Patent Application No. 1362978, filed Dec. 19, 2013, each hereby expressly incorporated by reference in its entirety and each assigned to the assignee hereof.

The invention relates to a topical pharmaceutical composition, dermatological in particular, and to use thereof for the prevention or treatment of rosacea and particularly erythematotelangiectatic rosacea.

Numerous inflammatory skin disorders often lead to unsightly, painful skin rashes, acne, telangiectasia and skin rashes similar to acne such as maculae, nodules and pustules which may weep and form scabs.

For example, rosacea is chronic inflammatory dermatosis chiefly affecting the central part of the face and eyelids of some adults. It is characterized by telangiectatic erythema, dryness of the skin, papules and pustules.

Rosacea generally develops in adults aged between 30 and 50 years; it most frequently affects women although the disorder is generally more severe in men. Rosacea is chronic and persists for many years with periods of exacerbation and remission.

Rosacea formerly known under the name « acne rosacea » is not a disorder of the pilosebaceous follicle as in adolescent acne but is primarily a vascular disorder having an inflammatory stage free of cysts and comedones characteristic of acne vulgaris.

The aetiology of rosacea still remains ill understood although numerous theories have been put forward. The most common theory is based on the characteristic presence of the parasite *Demodex folliculorum* in patients suffering from rosacea. Other factors have been described as possibly contributing towards the development of rosacea such as psychological, environmental factors (sun exposure, temperature, humidity) immunological, emotional (stress), dietary (alcohol, spices), hormonal, vascular factors, gastro-intestinal disorders even infection with *Helicobacter pilori*.

Rosacea can be classified as follows:
Type I: Erythematotelangiectatic rosacea, chiefly characterized by persistent central facial erythema and episodic reddening or flushes. Often this type is also characterized by oedema, rough patches and visible dilated blood vessels (telangiectasia) and burning, stinging sensations.
Type II: Papulopustular rosacea, characterized by persistent central facial erythema and the onset of transient, central facial papules or pustules resembling those of acne. These symptoms are at times accompanied by burning, stinging sensations. This type usually follows after Type I or combines therewith.
Type III: Phymatous rosacea distinguished by thickening of the skin and the onset of irregular nodules. Although the nose is the region most often affected becoming very large and covered with swellings ("rhinophyma"), other regions can also be affected: chin, forehead, cheeks and ears. This type usually follows after Type I and Type II or is combined therewith.
Type IV: Ocular rosacea. In this type of rosacea red, irritated eyes can water and appear to be injected with blood. The symptoms may comprise the feeling of having a foreign body in the eye, excessive tear-forming, sensitivity to light, blurred vision, sensations of burning, dryness, stinging, pruritus and alacrima. These can occur with or without rosacea. The onset may occur before, during or after the onset of cutaneous signs.

Current treatments which are directed towards control over rashes and redness, skin inflammation, have limited efficacy in numerous patients and in general can only be used over a limited period of time. Standard treatments include avoidance of pathology-potentiating factors such as sun exposure, wind exposure, alcohol consumption, spicy, irritant foods, cleansing lotions and cosmetics.

Conventionally rosacea is treated orally or topically with antibiotics such as tetracyclines, erythromycin, clindamycin, but also vitamin A, salicylic acid, antifungal agents, steroids, metronidazole (antibacterial agent) or isotretinoin in severe forms, or with anti-infection agents such as benzoyl peroxide or azelaic acid. Rosacea treatment is also known which uses ivermectin to target the parasite *Demodex folliculorum* found on the skin of patients (U.S. Pat. No. 5,952,372).

Rosacea is also known to be treated with agonists of alpha-1 or apha-2 adrenoceptors (US 2006/0171974, US 2005/0165079, US 2005/0020600). Brimonidine is a selective agonist of alpha-2 adrenergic receptors. Brimonidine has also proved to be useful in the treatment of rosacea and in particular the erythema caused by rosacea, see for example patent application US 2004/242588 by DeJovin et al.; application US 2005/020600 by Scherer; application US 2009/061020 by Theobald et al., or telangiectasia caused by rosacea, see for example patent application US 2006/0264515.

Unfortunately the use of these drugs such as antibiotics for example can often cause side effects and may generate intolerance problems in numerous patients. In addition, none of the existing treatments allows the efficient treatment and/or prevention of all the symptoms associated with rosacea over the long term.

Having regard to the foregoing, there is therefore a need for more efficient treatment of rosacea having extended efficacy over time, having fewer side effects, in particular a composition imparting greater tolerance of the active ingredient whilst reducing its side effects.

The Applicant proposes providing a topical pharmaceutical composition for the treatment of rosacea that is more efficient and having extended effect, in particular for erythematotelangiectasic rosacea (Type I), with potentially fewer side effects irrespective of length of application period. In particular, the treatment can be efficient over a longer time having a persistent effect after treatment has been stopped for several weeks even several months. This pharmaceutical composition can additionally prevent a rebound effect that is sometimes observed at the end of treatment.

The subject of the invention is a topical pharmaceutical composition comprising naratriptan or a pharmaceutically acceptable salt thereof in a pharmaceutically acceptable carrier for the treatment and/or prevention of rosacea and more preferably erythematotelangiectasic rosacea, (so-called Type I).

Preferably the composition of the invention is for the treatment of rosacea.

The invention relates to the use of naratriptan or pharmaceutically acceptable salt thereof for the preparation of a medicinal product administered via topical route intended for the prevention and/or treatment of rosacea and more preferably erythematotelangiectasic rosacea, so-called Type I.

A further subject of the present invention is a method to treat and/or prevent rosacea and more particularly to treat and/or prevent Type I rosacea, said method comprising the administration via topical route of a topical pharmaceutical composition comprising a therapeutically efficient amount of naratriptan or pharmaceutically acceptable salt thereof.

The invention further concerns naratriptan or pharmaceutically acceptable salt thereof administered via topical route for use in the treatment and/or prevention of rosacea, more preferably Type I rosacea.

The invention additionally relates to the use of naratriptan or pharmaceutically acceptable salt thereof for the preparation of a topical pharmaceutical composition, dermatological in particular, intended for the prevention and/or treatment of rosacea and in particular Type I rosacea.

The Applicant has surprisingly discovered that naratriptan or pharmaceutically acceptable salt thereof has combined properties in terms of action, safety and skin penetration making it a unique candidate for the treatment of rosacea via topical route. In particular, naratriptan exhibits stronger vasoconstrictor action on human vessels than the other members of the triptan family and very good neurogenic anti-inflammatory action thereby imparting efficacy in the prevention and/or treatment of rosacea and more particularly erythematotelangiectatic rosacea (or Type I). The action of naratriptan has been demonstrated on vessels taken from the human subcutaneous compartment. In man, each organ has a particular vascular tissue (arteries or veins) in terms of organisation, structure, tonicity and vascular reactivity. These properties are essentially due to type of receptor. For example, only skin vessels of small diameter express alpha 2 adrenoceptors whereas vessels of small, medium and large diameter express alpha 1 adrenoceptors. Contractile responses therefore differ as a function of selective activators or inhibitors of alpha 1 or alpha 2 adrenoceptors. It is therefore in theory impossible, without knowing the expression and location of a particular type of receptor, to predict the behaviour of skin blood vessels regarding the contraction or dilation thereof. This reasoning also applies to serotonin 5HT1B and D receptors, which in particular are activated by triptans. Surprisingly the Applicant has discovered first that 5HT1B triptan receptors are expressed on small blood vessels of diameter ranging from 200 to 500 μm (and 5HT1D triptan receptors are present on the ends of sensory nerves) and also that these vessels are more reactive to naratriptan compared with all the tested triptans. This discovery is all the less obvious since the physicochemical parameters of the different compounds of the triptan family are not predictive of action on the rosacea skin of patients.

Aside from this purely vasoconstrictive effect of naratriptan, the inhibited release of vasodilating neuropeptides may provide an additional benefit over the long term by significantly reducing neurogenic inflammation.

Neurogenic inflammation is a major component of Type I rosacea (erythematotelangiectatic). This process in which inflammation is triggered by the sensory nerve system is characterized by symptoms such as redness, swelling and heat. Different stimuli (temperature, hot or spicy beverages . . . ) are responsible for «flushes» and may lead to permanent facial erythema. On the face, these stimuli activate the trigeminal sensory nerve system locally releasing neuropeptides (CGRP, SP, PACAP . . . ). These neuropeptides then induce vasodilation, the cause of redness.

Therefore naratriptan, having regard to its action on the 5HT1D receptors, is capable of activating the receptors at the ends of the sensory nerves of the skin and of reducing neurogenic inflammation in the skin.

It therefore acts on flushes and/or erythema of rosacea in particular of Type I or 11. The effect of naratriptan is highly advantageous in obtaining extended efficacy of the treatment of rosacea, in particular of Type I or II.

In one preferred embodiment, the composition of the invention is used in the treatment of erythematotelangiectatic rosacea, or so-called Type I.

In one particular embodiment the composition of the invention is used for the treatment of papulopustular rosacea, or so-called Type II.

Naratriptan or N-methyl-2-[3-(1-methylpiperidin-4-yl)-1H-indol-5-yl]ethanesulfonamide belongs to the triptan family. This family of active ingredients is used in medications intended for acute treatment of migraine attacks. They are also used in the treatment of vascular facial pain. There are several types of triptans including sumatriptan, the first triptan to be marketed in the 1990s, naratriptan, zolmitriptan, eletriptan, almotriptan, frovatriptan and rizatriptan. They are in the form of various pharmaceutical preparations: injectable or self-injectable, oral forms or nasal spray.

The Applicant has surprisingly discovered that naratriptan is the best candidate in the triptan family for application via topical route in the treatment of rosacea, based on its efficacy, safety and skin penetration. Frovatriptan, zolmitriptan and eletriptan are suspected of being genotoxic and carcinogenic, and sumatriptan generates eye disorders in particular corneal opacification. Rosacea is considered to be a benign dermatological disease although its most advanced, severe forms may have major morbidity for patients. Nevertheless the benefit/risk ratio for treated patients must be extremely high. These latter compounds (frovatriptan, zolmitriptan, eletriptan, sumatriptan) show potential for systemic toxicity after topical administration and as a result they are very poor candidates for a topical rosacea product. Rizatriptan on the other hand, on account of its pharmacokinetic parameters, generates potential problems of drug interactions and generates an active metabolite which represents 14% of the parent molecule leading to complications for development thereof.

Only naratriptan and almotriptan exhibit a satisfactory safety profile.

In general, over and above the action and non-toxicity of compounds for use in rosacea via topical route, there is another essential property required to guarantee efficacy of the compound: this is the penetration of the compound into the skin through its different layers to reach the pharmacological targets. Regarding rosacea these targets (5HT-1B and D receptors) are located both on the vessels of the dermis and on the nerve endings of the dermis and epidermis. This penetrating property is critical and indispensable for a compound applied via topical route. It combines with the properties of intrinsic action of the compound to guarantee its clinical efficacy in the treatment of a skin disorder. If there is little or no skin entry the compound will be fully ineffective clinically for treatment of the pathology via topical route.

The Applicant has surprisingly discovered that naratriptan shows much better penetration into human skin than almotriptan. In particular, the total amount of naratriptan found in human skin after topical application of a formula at 2% concentration in a phosphate buffer solution (PBS) is almost twice the amount of almotriptan found when used in PBS at the same concentration (3.46% vs. 1.86%). This favourable property of natratriptan is particularly unexpected. Especially as it is impossible to predict which compound will show the most favourable penetration simply on the basis of its chemical structure and/or physicochemical profile.

The efficacy on small diameter blood vessels and the skin penetration of naratriptan, both higher than those of other triptans, and its good safety profile give this compound an unequalled profile for the treatment of rosacea via topical route.

The expression "pharmaceutically acceptable salt(s)" in the present context designates the salts of a compound of interest, preferably for topical use in mammals, and which have the desired biological activity. Pharmaceutically acceptable salts comprise salts of acid or basic groups contained in the specified compounds. Pharmaceutically acceptable acid addition salts comprise, but are not limited to, the following: hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, ptoluenesulfonate and pamoate (i.e. 1,1'-methylene-bis-(2-hydroxy-3-naphthoate)). Adapted base salts include but are not limited thereto: aluminium, calcium, lithium, magnesium, potassium, sodium, zinc and diethanolamine salts. For a review of pharmaceutically acceptable salts see Berge et al. (J Pharm Sci. 1977 January; 66(1):1-19).

In one preferred embodiment the naratriptan salt is a naratriptan hydrochloride.

By topical application is meant the applying or spreading of the composition of the invention over the surface or the skin or mucosa.

The compositions of the invention further comprise a pharmaceutically or cosmetically acceptable carrier i.e. a carrier adapted for topical use in contact with human cells, free of toxicity, intolerance, irritation, undue and similar allergic response and in proportion to a reasonable benefit/risk ratio.

In the remainder of the text the term naratriptan is used indifferently to define naratriptan or one of the salts thereof.

The compositions of the invention may also comprise any additive or adjuvant usually used in the pharmaceutical and more particularly dermatological field that is compatible with naratriptan.

Evidently persons skilled in the art will take care to ensure that this or these optional compounds and/or their amount are chosen so that the advantageous properties of the composition of the invention are not or are not substantially deteriorated.

The compositions of the present invention can be in any preparation form normally used for topical application, in particular in the form of solutions, lotions, gels, unguents, emulsions of liquid or semi-liquid consistency of milk type obtained by dispersion of an oil phase in an aqueous phase (O/W) or conversely (W/O), or powders, impregnated pads, sprays, suspensions or emulsions of soft, semi-liquid or solid consistency of cream or ointment type. These compositions are prepared following usual methods.

Advantageously the composition comprises an ointment, cream, lotion or gel.

In one embodiment the term "treatment" or "to treat" designates an improvement, prophylaxis of a disease or disorder, or at least of a discernible symptom thereof.

In another embodiment, "treatment" or "to treat" designates an improvement, prophylaxis of at least one measurable physical parameter associated with the disease or disorder being treated, which is not necessarily discernible in or by the treated subject.

In another additional embodiment, "treatment" or "to treat" designates inhibition or slowing of progress of a disease or disorder physically e.g. by stabilisation of a discernible symptom, or physiologically e.g. by stabilisation of a physical parameter, or both.

In another embodiment "treatment" or "to treat" designates delayed onset of a disease or disorder.

In some embodiments, the compound of interest is administered as a preventive measure. In the present context "prevention" or "to prevent" designate a reduction in the risk of acquiring a specified disease or disorder.

In the meaning of the present invention by « patient» is meant any mammal and more particularly human beings, men or women.

The actual amount of naratriptan administered is dependent on the desired therapeutic effect, and may therefore vary to a large extent. Therefore, and according to one preferred embodiment, the pharmaceutical composition is administered once to twice daily. Preferably the treatment may last from 1 week to 6 months, renewable, and preferably 2 weeks to 4 months.

Courses of treatment can be cyclically renewed with or without a rest period.

In the compositions of the invention, naratriptan is contained in the composition at a concentration between 0.0001% and 5% by weight relative to the total weight of the composition in which it is contained, preferably between 0.001% and 3% by weight relative to the total weight of the composition.

In this entire text, unless otherwise specified, the ranges of concentration indicated include the upper and lower limits of said range.

Other aspects and advantages of the invention will become apparent on reading the following examples which are to be construed as illustrative and non-limiting.

KEYS TO FIGURES

FIG. 1: Effect of naratriptan on vascular tonicity of human subcutaneous veins ex-vivo as a function of time.

Figure 2:
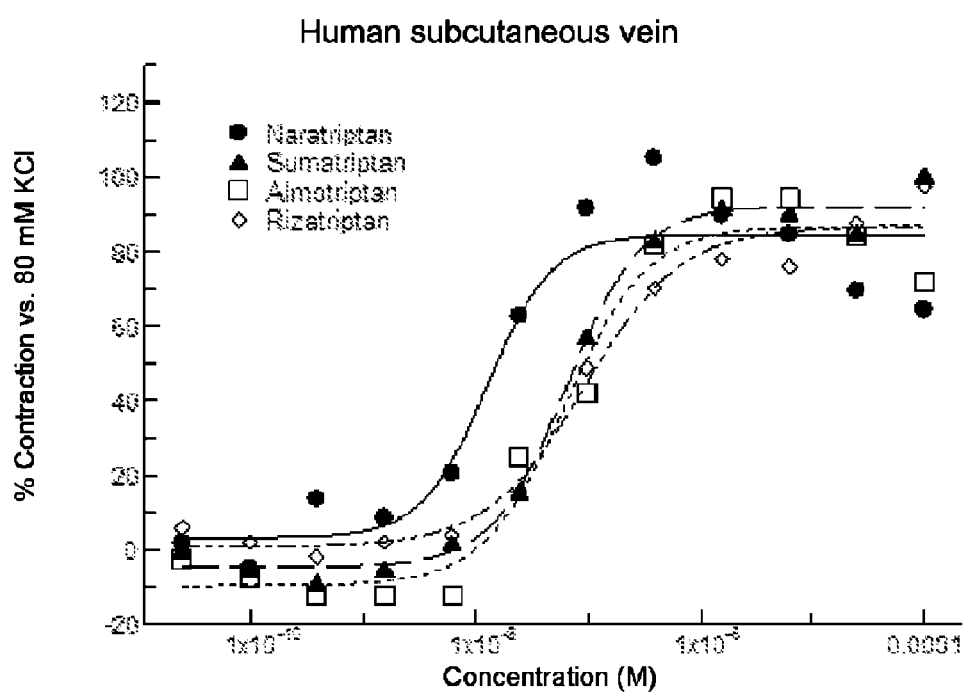

FIG. 2: Effect of four triptans on vascular tonicity of human subcutaneous veins, ex-vivo.

Figure 3:
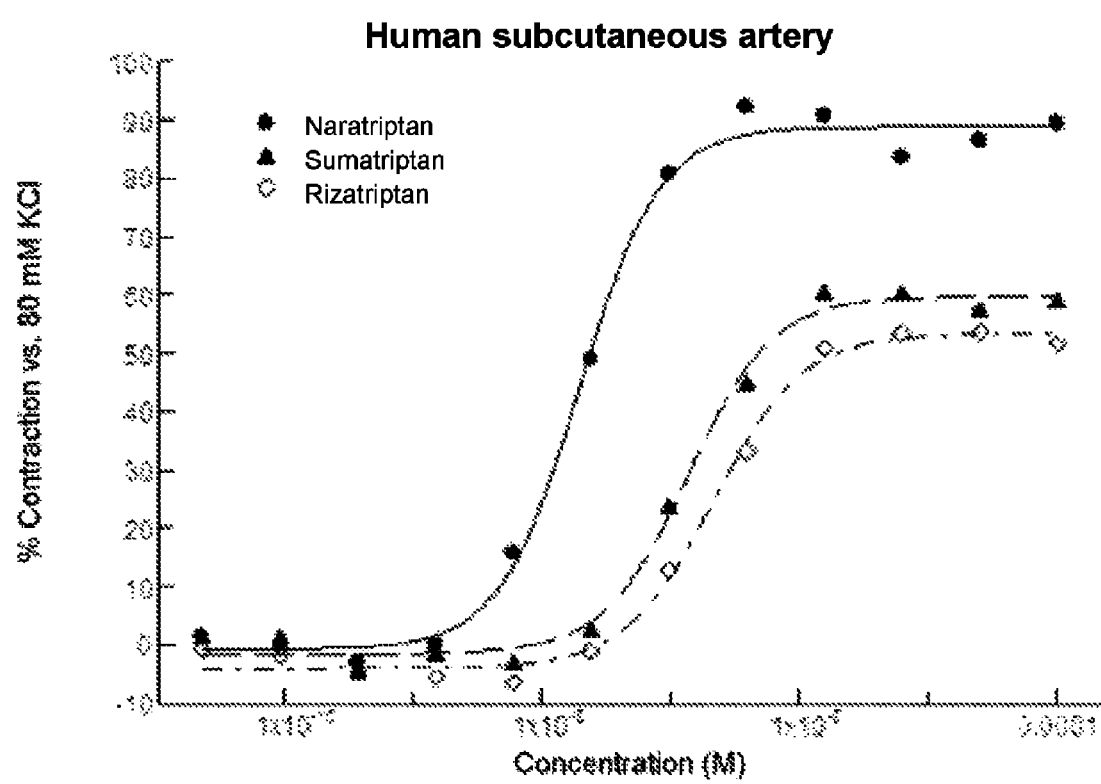

FIG. 3: Effect of four triptans on vascular tonicity of human subcutaneous arteries, ex-vivo.

EXAMPLES

Example 1: Evaluation of the Effect of Naratriptan on Vascular Tonicity of Human Subcutaneous Veins, Ex Vivo Via Myography Technique The dose-response effect of naratriptan hydrochloride was evaluated on isolated human subcutaneous veins, by measuring tension on vessel contraction ex-vivo using the myography technique.

Material and Methods

Human subcutaneous veins are isolated from healthy human skin derived from plastic surgery operative waste (abdominal plasty). On receipt the skin sample is held at 4° C. in a receptacle containing physiological saline solution (PSS) 1× at pH=7.4. Dissection, isolation and mounting of the veins are conducted in cold PSS pH=7.4 using straight forceps and a stereomicroscope. Once the vein is isolated and cleaned of surrounding fat and conjunctive tissue, a segment 2 mm in length and diameter of between 100 and 600 µm is mounted in the myograph chamber between two 40 µm tungsten wires attached to removable jaws connected to the tension sensor and held in physiological saline solution (PSS) at pH=7.4 and 37° C. To perform the myography study the vein is placed at working pre-tension (g) corresponding to physiological pressure of 18 mmHg. Pre-tensioning is obtained by mechanical action to draw apart the tungsten wires (40 µm). The viability of the vessel is verified by depolarising the membrane of the vessel smooth muscle cells by increasing the concentration of potassium in the chamber. To do so the PSS solution contained in each chamber is replaced by a solution containing 80 mM KCl at pH=7.4 and pre-heated to 37° C. This step must be repeated twice with 1×PSS washing to cause relaxation between each contraction. At this stage if there is no change in measured tension the isolated vessel is considered non-viable. Naratriptan was evaluated by dose-response (n=1) to determine its maximum contraction intensity (Emax) and strength (EC50). The vessel was treated with increasing successive doses of product added every 3 minutes to the myograph chamber. Tension data (g) are successively converted to:

Tension (mN) 1 g=9.81 mN

Tension applied to the vessel wall (mN/mm): by dividing the tension value in mN by twice the length of the vessel i.e. 4 mm.

Data are then expressed for the vasoconstrictor product in percentage contraction (%) taking as 100% the value obtained for treatment with 80 mM KCl at step 1 to verify vessel viability.

Results

FIG. 1 shows visualisation of raw data obtained during dose-response evaluation of naratriptan. The tension (g) measured by the sensor is given as a function of time. The vessel can be seen to contract by adding increasing doses of the compound every 3 minutes, followed by successive washings at the end of the study. Therefore a first washing of the chamber is performed 3 minutes after adding the maximum dose of product to the myograph chamber (removal of product). At this step and with no vasoconstrictor compound in the chamber, the vessel should relax spontaneously until it returns to its normal or physiological vascular tonicity. As illustrated in FIG. 1, relaxing of the vessel is very slow and even impossible after contraction caused by naratriptan. It can also be seen that after several successive washings the vessel tends to re-contract until it reaches the maximum contraction intensity obtained with KCl, although it is no longer in the presence of the tested compound. Naratriptan exhibits a persistent effect on the human vein after several successive washings up until 90 minutes after removal of the compound from the chamber.

These results show that the contraction induced by naratriptan is sustained over time, this being highly advantageous for treatment of rosacea.

Example 2: Evaluation of the Effect of 4 Triptans on the Vascular Tonicity of Human Subcutaneous Blood Vessels (Vein and Artery) Ex Vivo Via Myography Technique Material and Methods The method used for this study is identical to the method used in Example 1. To perform myographic studies the vein is placed at a pre-tension (g) corresponding to physiological pressure of 18 mmHg while the artery is placed at a pre-tension of 90 mmHg since an artery wall is thicker than a vein wall.

The myograph apparatus has four independent chambers. Therefore four vessel segments were mounted in parallel in each study. Each compound was subjected to dose-response evaluation for each type of vessel (n=1). The vessel was therefore treated with successive, increasing concentrations of product added every 3 minutes to the myograph chamber. The tested compounds were naratriptan, sumatriptan, almotriptan and Rizatriptan.

Only three compounds (naratriptan, sumatriptan and rizatriptan) were able to be evaluated in this study on the arteries since the response of the artery mounted in chamber 2 proved to have low intensity at the first « quality » control step when treated with 80 mM KCl.

Results:

Contraction intensity and the strength (EC50) of each compound are given in the Table below.

| Compound | Human subcutaneous artery | | Human subcutaneous vein | |
|---|---|---|---|---|
| | EC50 (nM) | Emax (% max. contraction vs. 80 mM KCl) | EC50 (nM) | Emax (% max. contraction vs. 80 mM KCL) |
| Naratriptan | 20 | 82 | 13 | 105 |
| Sumatriptan | 138 | 61 | 65 | 101 |
| Almotriptan | Non-determined | Non-determined | 62 | 97 |
| Rizatriptan | 217 | 54 | 93 | 94 |

On Veins:

The results obtained show that the compounds induce dose-dependent vasoconstriction of the human subcutaneous vein (FIG. 2).

Naratriptan shows strong vasoconstrictor potential (EC50=13 nM) with maximum intensity (Emax) of 105% on the human subcutaneous vein, higher than the values obtained with the other triptans.

On the Arteries:

The results obtained show that the compounds also induce dose dependent vasoconstriction of the human subcutaneous artery (FIG. 3). The results obtained with sumatriptan (EC50=138 nM; Emax=70%) tally with those described in the literature (Gupta et al., J Hypertens. 2006 July; 24(7): 1345-53).

Maximum contraction intensity on the artery is obtained with naratriptan (Emax=82%). The latter is also the most powerful vasoconstrictor (EC50=20 nM).

Among the 4 evaluated triptans, naratriptan therefore exhibits the best activity in terms of strength and efficacy both on human subcutaneous veins and arteries.

Example 3: Neurogenic Inflammation Assay

Neurogenic inflammation induced in mouse ear after a single application of reziniferatoxin (RTX) is significantly inhibited with 1% naratriptan for up to 45 minutes after treatment in the acetone carrier. The compound was then tested in a water/ethanol carrier to increase solubility. The candidate showed significant inhibition of neurogenic inflammation after application at 1% via topical route after a treatment time of 15 minutes.

Example 4: Efficacy of Naratriptan in Patients Suffering From Rosacea

A randomised, double-blind, intra-individual study in 25 subjects suffering from Type I rosacea was conducted. This study comprises a maximum selection period of 4 weeks, a treatment period of 4 weeks and a follow-up period of 2 to 4 weeks.

To examine the issue of systemic exposure and efficacy, two regions are treated with naratriptan once a day for 4 weeks: a semi-facial region and an equivalent surface area on the back. This provides maximised conditions for rosacea in terms of application surface. The two other symmetric regions on the face and back are treated with the carrier.

Clinical evaluations of erythema (erythema score scale), flushes (frequency and response in an induced flush model) and biophysical evaluations (colorimetry and photographs) are calculated for the face. Skin penetration and pharmacodynamic measurements can be performed on the backs of subjects by tape-stripping and/or biopsies. The general safety and local tolerance of the product are evaluated throughout the study (onset of adverse events, biological results, heart monitoring, evaluation of irritation, etc. The follow-up period at the end of treatment is 2 to 4 weeks.

Example 5: Comparison Between Naratriptan and Almotriptan Human Skin Penetration Study on the release and penetration into «dermatomized» human skin (Franz cells) showed that the 2 molecules at 2% in PBS are capable of reaching their target, but that a much higher amount of naratriptan is found in total human skin compared with almotripan.

Table summarizing data of the release/penetration study:

|  |  | Naratriptan hydrochloride | | Almotriptan maleate | |
|---|---|---|---|---|---|
|  |  | Mean | Standard deviation | Mean | Standard deviation |
|  | Amount applied | 184.37 | 1.46 | 151.18 | 1.03 |
| Non-absorbed | $\mu g/cm^2$ | 162.40 | 2.89 | 139.88 | 0.86 |
|  | % applied dose | 88.08 | 1.53 | 92.53 | 0.64 |
| Stratum corneum | $\mu g/cm^2$ | 3.17 | 0.36 | 1.50 | 0.54 |
|  | % applied dose | 1.72 | 0.20 | 0.99 | 0.40 |
| Epidermis | $\mu g/cm^2$ | 2.95 | 0.83 | 0.97 | 0.37 |
|  | % applied dose | 1.60 | 0.45 | 0.64 | 0.27 |
| Dermis | $\mu g/cm^2$ | 0.53 | 0.15 | 0.34 | 0.11 |
|  | % applied dose | 0.29 | 0.08 | 0.23 | 0.08 |
| Absorbed dose | $\mu g/cm^2$ | 0.03 | 0.02 | 0.02 | 0.02 |
|  | % applied dose | 0.02 | 0.01 | 0.01 | 0.01 |
| Total penetrated amount | $\mu g/cm^2$ | 6.37 | 1.39 | 2.86 | 1.03 |
|  | % applied dose | 3.46 | 0.76 | 1.89 | 0.74 |
| Mass balance | % applied dose | 91.22 | 2.59 | 94.16 | 1.59 |
| Total skin | % applied dose | 3.61 |  | 1.86 |  |

To conclude, naratriptan is proposed herein for its efficacy on erythema and flushes whilst being well tolerated. Naratriptan is useful for the treatment of rosacea and particularly of erythema found in erythematotelangiectatic and papulopustular rosacea, and more particularly Type I rosacea.

This effect can persist for several days even several weeks after discontinuation of naratriptan application, preventing the re-onset of erythema.

The invention claimed is:

1. A topical pharmaceutical composition for the treatment of rosacea, wherein the topical pharmaceutical composition comprises from 1% to 5% by weight of naratriptan or pharmaceutically acceptable salt thereof, in a pharmaceutically acceptable carrier, wherein the naratriptan or salt thereof has about five times stronger vasoconstrictor action on human vessels than other members of the triptan family.

2. The composition according to claim 1, wherein the rosacea is Type I or II rosacea.

3. The composition according to claim 1, wherein the rosacea is Type I rosacea or erythematotelangiectatic rosacea.

4. The composition according to claim 1, wherein the composition comprises naratriptan hydrochloride.

5. The composition according to claim 1, wherein the composition is in the form of an ointment, cream, lotion or gel.

6. A method of preparing a medicinal product to typically treat rosacea, the method comprising preparing the composition according to claim 1, comprising an effective amount of naratriptan or pharmaceutically acceptable salt thereof.

7. The method according to claim 6, wherein the rosacea is Type I rosacea or erythematotelangiectatic rosacea.

8. The method according to claim 6, wherein the composition comprises naratriptan hydrochloride.

9. The method according to claim 6, wherein the concentration of naratriptan or salt thereof is from 0.0001% to 5% by weight relative to the total weight of the composition.

10. A method of treating rosacea, the method comprising administering to an individual subject in need thereof an effective amount of pharmaceutical composition according to claim 1.

11. The method according to claim 10, wherein the naratriptan or salt thereof are typically administered in a composition comprising the naratriptan or salt thereof and a pharmaceutically acceptable carrier.

12. The method according to claim 10, wherein the rosacea is Type I or II rosacea.

13. The method according to claim 10, wherein the rosacea is Type I rosacea or erythematotelangiectatic rosacea.

14. The method according to claim 11, wherein the composition comprises naratriptan hydrochloride.

15. The method according to claim 11, wherein the concentration of the naratriptan or salt thereof is from 0.0001% to 5% by weight relative to the total weight of the composition.

16. The method according to claim 11, wherein the composition is in the form to an ointment, cream, lotion or gel.

* * * * *